United States Patent [19]

Wardlaw et al.

[11] 4,077,396
[45] Mar. 7, 1978

[54] MATERIAL LAYER VOLUME DETERMINATION

[76] Inventors: Stephen Clark Wardlaw, 16 Pine Orchard Rd., Branford, Conn. 06405; Robert Aaron Levine, 31 Pilgrim La., Guilford, Conn. 06437; James Vincent Massey, III, 80 Driftwood La., Trumbull, Conn. 06610

[21] Appl. No.: 746,935

[22] Filed: Dec. 2, 1976

Related U.S. Application Data

[63] Continuation-in-part of Ser. No. 673,058, Apr. 2, 1976, Pat. No. 4,027,660.

[51] Int. Cl.² ............................................. A61B 5/14
[52] U.S. Cl. .............................. 128/2 F; 73/425.4 P; 73/149; 128/DIG. 5; 128/2 G; 210/83; 210/DIG. 23
[58] Field of Search ....... 128/2 F, 2 G, 2 W, DIG. 5; 73/149, 444, 425.4 P; 233/1 R, 26; 210/78, 83, DIG. 23, 24

[56] References Cited

U.S. PATENT DOCUMENTS

| 2,398,737 | 4/1946 | Elliot et al. | 73/425.4 P X |
| 3,437,266 | 4/1969 | Patterson | 210/78 X |
| 3,508,653 | 4/1970 | Coleman | 233/26 X |
| 3,513,976 | 5/1970 | James | 210/78 |
| 3,647,070 | 3/1972 | Adler | 210/83 |
| 3,898,982 | 8/1975 | Katsuda | 128/2 F |
| 3,920,557 | 11/1975 | Ayres | 128/2 F X |

FOREIGN PATENT DOCUMENTS

| 2,243,569 | 3/1973 | Germany | 233/1 R |
| 1,391,053 | 4/1975 | United Kingdom | 128/2 G |

Primary Examiner—Kyle L. Howell
Attorney, Agent, or Firm—William W. Jones

[57] ABSTRACT

A technique for generally determining the approximate volume of the white cell and platelet layers in a centrifugally separated mixture of anticoagulated blood. A centrifuge tube is used to hold the blood sample and an appropriately shaped body is disposed in the tube in the zone occupied by the white cell and platelet layers whose volume is to be measured. The body reduces the available volume within the tube which may be occupied by the white cell and platelet layers and thus expands the axial extent thereof to make visual measurement of the white cell and platelet layers more accurate. The body has an inwardly and upwardly tapered upper end portion which prevents platelet cells from aggregating on the top of the body.

3 Claims, 3 Drawing Figures

MATERIAL LAYER VOLUME DETERMINATION

This application is a continuation-in-part of co-pending application Ser. No. 673,058, filed Apr. 2, 1976, now U.S. Pat. No. 4,027,660.

This invention relates to a technique for enabling quick visual measurement of the approximate volume of a constituent material layer in a centrifuged material mixture. More particularly, this invention employs a body disposed in a centrifuge tube within the general confines of the layer to be measured and which acts to elongate the axial extent of the volume occupied by the layer to be measured.

Various techniques have been proposed for use in measuring the volume of a constituent layer of material within a material mixture, which material mixture has been centrifuged to separate out the various constituent materials into layers according to density, or specific gravity. These techniques have found particular application in measuring the several constituents of various biological fluids, such as blood, for example.

The particular blood constituent which has proven to be most difficult to quickly and easily measure is the buffy layer, which is made up of the various white cell types and platelets. In a centrifuged anticoagulated whole blood sample, the buffy layer is located between the red cell layer and the plasma layer, but because of the relative paucity of the buffy layer, a quick visual technique for measuring the buffy layer has, heretofore, been lacking.

One technique for determining the white cell count involves the use of a precisely measured volume of whole blood which is precisely diluted and placed in an optical counting chamber of a given volume. The diluted blood sample is then examined with a microscope and the leukocytes or white blood cells are visually counted. This technique is time consuming, requires relatively expensive equipment, and is subject to errors arising from inaccurate sample measurement and imprecise sample dilution.

Another technique has been devised for the automatic measurement of the leukocyte count of a blood sample. The sample of whole blood is manually or automatically diluted and the white cells are counted either by detecting and measuring light scatter from them in the sample as they pass through a confined space, or by measuring their effect on an electrical field as they pass through a small aperture. These automated techniques are quite accurate, but the equipment needed is quite expensive. The equipment also requires specially trained technicians to be used.

In the more general field of the volumetric measurement of constituent material layers in a centrifuged material mixture, it has been proposed to physically enlarge the axial extent of the layer of interest in order to perform some further operation on the layer. Specifically, it is proposed in the prior art to provide a specially formed flask for use in determining the leukocyte count in a whole blood sample. The flask is a centrifuge vessel and includes a mid-axial area of constricted internal diameter which, because of its reduced volume, will form a narrow vertical volume of leukocytes. A high density material, such as mercury, must be used in this flask to raise the blood sample so as to ensure that the leukocytes occupy the narrow mid-axial neck of the vessel. Once properly positioned, the leukocytes are aspirated out of the vessel and subjected to further testing. It will be appreciated that such a flask is difficult to accurately form, is quite fragile, and cannot be readily used as a capillary tube due to the necessity of having one end closed to facilitate the introduction of the mercury thereinto. This flask thus is used for relatively large blood samples and the harvesting of leukocytes therefrom only.

Another proposal for centrifugal separation enhancement is set forth in the prior art. This latter technique involves the use of closely packed artificially produced microspheres which are disposed within a centrifuge tube to restrict the free volume available to be occupied within the tube by the centrifuged fluid material. The microspheres are formed with a plastic core having a metallic coating for accurately controlling the overall sphere density. Sphere densities, in turn, are selected so that a plurality of spheres will float in each layer of the centifuged materials. Thus each material layer will have its particular density equal to the density of an associated plurality of spheres, which spheres, by reason of the density gradient of the centrifuged mixture, will be restricted to and "float in" the particular material layer of the same density. In this manner the axial extent of each layer will be expanded for easier visual measurement. The spheres of different densities can also be of different colors to further contrast the several layers each from the others. This technique has several problems one of which relates to centrifugation in general, i.e. the problem of how to get the spheres into the tube, especially if the tube is of capillary size, and the other of which relates to its use in a buffy layer measuring technique. This latter problem arises from the packing characteristics of spheres wherein the resultant free space available to be occupied by the buffy layer is about 33% of the original free space present without the spheres. This means that the axial extent of the buffy layer in a centrifuged blood sample can only be increased about threefold using microspheres alone, and this degree of increase is insufficient to permit simple, visual measurement of the volume of the buffy layer with any acceptable degree of accuracy.

In order to provide a quick, inexpensive visual technique for determining the general buffy layer measurement or leukocyte count in an anticoagulated blood sample, we propose the use of at least one axially elongated volume-occupying mass which is made of a material having a specific gravity such that the mass will float upon, or slightly in the red cell layer of the centrifuged blood sample. The mass is disposed in the capillary tube bore, has its axis of elongation substantially coincidental with the tube bore axis and combines with the tube bore to form an axially extending free space between the tube bore wall and the exterior of the mass. The volume of the free space is substantially less than the free volume of the tube bore so that the axial extent of the buffy layer will be markedly increased when the buffer layer is positioned in the free space during and after centrifugation.

We have discovered that the upper end portion of the mass should be formed with an inwardly tapered configuration, such as conical or ogival to prevent the platelet cells from aggregating on top of the mass, the platelet cells being the lightest cells in the buffy layer. Thus all of the platelet cells collect in the restricted free volume wherein their extent can be measured.

It is, therefore, an object of this invention to provide a technique for use in visually determining the general leukocyte and platelet count which make up the buffy layer in a sample of whole blood.

It is a further object of this invention to provide a technique of the character described which entails the use of a capillary-type centrifuge tube containing an axially elongated volume-occupying mass selectively positioned in the buffy layer and floating on the red cell layer of the blood sample.

It is yet another object of this invention to provide a technique of the character described which utilizes expendable paraphenalia and can be performed quickly in a doctor's office by relatively untrained personnel.

It is yet another object of this invention to provide a technique of the character described for performing a differential white cell and platelet count.

It is an additional object of this invention to provide a technique of the character described which is relatively accurate, and inexpensive to use.

It is a further object of this invention to provide a technique of the character described wherein the mass is shaped so as to assure that all of the platelet cells settle into the free volume means within the tube so that they may be accurately measured.

These and other objects and advantages of the invention will become more readily apparent from the following detailed description of several embodiments of the invention taken in conjunction with the accompanying drawings in which.

Figure 1:
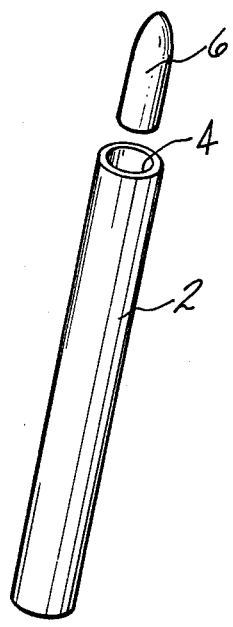
FIG. 1 is an exploded perspective view of one embodiment of an apparatus usable in determining the leukocyte or white cell and platelet count in accordance with the invention.

Referring now to the drawings, there is shown in FIG. 1 one embodiment of an apparatus which can be used in accordance with the invention for making a visual determination of the approximate white cell and platelet count in a sample of whole blood. The apparatus includes a capillary tube 2 of conventional construction having a through bore 4 which is open at both ends of the tube 2. An axially elongated volume-occupying mass 6 is positioned inside of the tube bore 4. In the embodiment shown in FIG. 1, the mass 6 takes the form of a right cylindrical insert or plug which is composed of a material having a predetermined specific gravity which renders the mass buoyant upon the centrifuged red cell mass. Due to its shape, the insert 6 will be held in the tube bore 4 so that both have substantially coincidental axes at all times. The diameter of the insert 6 is sufficiently smaller than the diameter of the tube bore 4 so as to be slidable within the tube bore 4 so that the insert 6 can gravitate to the red cell layer during centrifugation of the blood sample and float upon the red cell layer after centrifugation. The upper end portion of the insert is inwardly tapered like the ogive nose of a bullet at 8 so that the platelet cells will not aggregate on top of the insert and will all settle into the free space described hereinafter for accurate measurement.

The difference between the respective diameters of the insert 6 and tube bore 4 will form a free space of restricted volume, which free space is occupied by the centrifuged layer of white cells and platelets. By restricting the size of the free space available to the buffy layer, the apparent height or thickness of the buffy layer will be expanded over that obtained in an unrestricted capillary tube bore. Changes in the volume of the buffy layer from sample to sample will thus be "magnified" so that one can visually determine whether the white cell and platelet count is high, low, or average, generally speaking. This general determination can then be used to indicate whether further more sophisticated tests are needed. It will be appreciated that the degree of expansion of the height of the buffy layer can be varied by varying the difference between the diameters of the insert 6 and tube bore 4. Expansion factors in the range of 4 up to 20 may be obtained. For example, an expansion factor or multiple of nine is readily obtained. It will be appreciated that this apparent expansion of the buffy layer is the result of the fact that the insert 6 occupies volume within the tube adjacent to the red cell layer, and thus reduces the free volume available to the buffy layer by a multiple of 0.75 or more.

Figure 2:
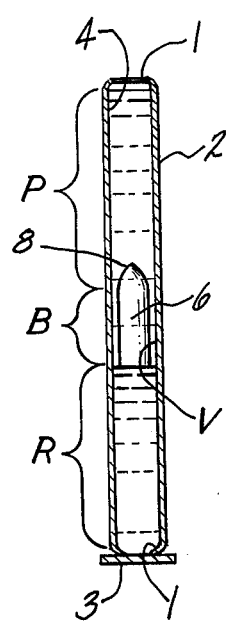
FIG. 2 is an axial sectional view of the apparatus of FIG. 1 as it is employed to make a visual measurement of the white cell and platelet count in a centrifuged whole blood sample.

Referring now to FIG. 2, there is shown the apparatus of FIG. 1 used to axially elongate the bounds of the buffy layer B. The sample has been centrifuged in the tube 2 with the volume-occupying mass insert 6 in place within the tube bore 4. As can be noted from FIG. 2 and as previously described, the tube bore 4 and the side surface of the insert 6 combine to form an annular free volume V directly above the red cell layer R into which annular free volume the buffy layer settles during centrifugation. It will also be noted that the annular free volume V is substantially smaller than a corresponding free volume within the tube bore, and thus the axial extent of the buffy layer occupying the annular free volume is substantially expanded. In other words, the distance between the upper and lower menisci of the buffy layer is increased. A minimum expansion multiple of about four is considered to be useful in visual white cell and platelet count determination in accordance with this invention. Relatively precise measurements of the axial dimension of the buffy layer by the use of mechanical, optical or electrical means can be made from the apparatus of FIG. 2.

The apparatus of FIGS. 1 and 2 is used as follows. The insert 6 is positioned inside of the tube bore 4 and the ends of the tube 2 may be inwardly crimped as at 1 to retain the insert within the bore, or the insert may be adhered to the wall of the tube bore by means of a blood-soluble adhesive such as gum acacia. The tube is then used in a conventional manner to draw a blood sample from a patient by means of a finger prick or otherwise. The anticoagulated drawn sample is then centrifuged with the resultant separation and elongation of the buffy layer as shown in FIG. 2.

It will be noted that the axially elongated shape of the insert 6 lends itself to formation thereof by injection molding of a resinous melt. The insert 6 is made of a material or materials having a specific gravity in the range of 1.02 to 1.09, and preferably about 1.04 gm/cc so that the insert 6 will be buoyant upon the red cell layer and yet sink through the buffy layer. Examples of such a material are acrylonitrile butadiene styrene (ABS), "commercial" styrene, and MMA styrene copolymer. A layering of different density materials may also be used to form the insert so long as the cross-sectional bulk density of the layered insert is an appropriate value.

The shape of the insert 6 shown in FIGS. 1 and 2 is right cylindrical with an upper ogive tapered end portion. The taper is used to prevent the platelet cells from aggregating on top of the insert and ensures that all of the platelets pass into the free volume where they will be measured.

Figure 3:
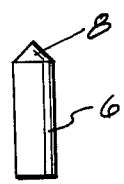
FIG. 3 is a side elevational view of another embodiment of the volume-occupying body.

FIG. 3 discloses an insert 6 which is provided with an upper end portion 8 which is cone-shaped so as to ensure that the platelets do not aggregate on top of the insert 6.

As previously noted, with the use of an axially elongated volume-occupying mass in the tube bore, axial elongation of the layer being measured can be increased by a multiple in the range of 4 to about 20. When determining white cell and platelet count in a blood sample, the preferred range of axial elongation of the white cell layer is a multiple in the range of about five to about fifteen.

It has been discovered that when an axial elongation of the buffy layer is produced within the preferred range, the layering by specific gravity of the individual components of the buffy layer, e.g. the polymorphonuclears, the mononuclear cells including lymphocytes, monocytes, and platelets will occur. The buffy layer components will layer as follows in order of lessening specific gravity, the polys, then the monos and lymphocytes (in the same layer), and lastly the platelets.

As previously noted, when the volume-occupying insert is formed from a material of the proper specific gravity and has an appropriate axial dimension, the insert will settle slightly into the upper portion of the red cell layer of the centrifuged blood sample. It is in this portion of the red cell layer that the reticulocytes, or immature red cells, layer out during centrifugation. Thus the insert will cause axial elongation of the reticulocyte sub-layer of the red cell layer. It has been discovered that an approximate reticulocyte count can also be made with the addition of a fluorescent strain to the blood sample. This count is useful to the physician in determining the rate of production of new red blood cells by a patient.

To observe this internal layering of the buffy layer, and the reticulocyte layer a fluorescent stain, such as Acridine orange, or the like, is added to the sample prior to centrifugation. The stain will be absorbed to varying degrees by the different constituents of the buffy layer, and by the reticulocytes and thus when exposed to fluorescent light, the various layers will fluoresce to different degrees. Thus the thickness of each sub-layer within the buffy layer and the thickness of the reticulocyte layer can be observed by illuminating the tube with light of the proper wavelength. If desired, optical magnification may be used to observe this layering. The stain may be coated on the tube bore wall, may be coated on the insert, or may be inserted into the tube bore in the form of a self sustaining, but soluble mass. For use with non-anticoagulated blood, an anticoagulant such as heparin can be added in the same manner to the blood sample. It will thus be appreciated that this invention makes possible a quick, simple visual differential white cell and platelet count and a reticulocyte count through the use of an appropriate fluorescent stain additive and a suitable light source, both of which may be readily available in a doctor's office.

An apparatus formed in accordance with this invention which will provide a nine fold axial expansion of the distance between the upper and lower menisci of the buffy layer in a sample of centrifuged whole blood includes a capillary centrifuge tube having an internal bore diameter of 0.05575 in. The volume-occupying mass is a right cylinder made from Rexolite, which is a cross-linked styrene having a specific gravity of 1.043, and having a diameter of 0.053 in. and a height of about ½ in.

It will be appreciated by those skilled in the art that this invention will enable visual or mechanical determination of the white cell and platelet count in a centrifuged sample of whole blood to be made at a low cost and quickly. With proper buffy layer expansion, a differential white cell and platelet determination can be made by using the apparatus and method of this invention. The apparatus of this invention is such that it can be prepackaged and can take the form of inexpensive disposable paraphenalia. Expensive and time consuming cell counters are not required to practice the technique of this invention.

Since many changes and variations of the disclosed embodiments of the invention may be made without departing from the inventive concept, it is not intended to limit the invention otherwise than as required by the appended claims.

What is claimed is:

1. For use in measuring the approximate white cell and platelet count in a centrifuged sample of whole anticoagulated blood, an apparatus comprising: a transparent tube for containing the centrifuged blood sample; at least one volume-occupying body formed from a material having a specific gravity in the range of about 1.02 to about 1.09 and disposed in said tube, said body being elongated along an axis which is substantially coincidental with the tube axis, said body being buoyant upon the red cell layer of the centrifuged blood sample, and said body being sufficiently movable within the tube so as to settle onto the red cell layer during centrifugation, said body being radially sized so as to form completely externally of said body a constricted free volume means adjacent to an inner surface of said tube and visible therethrough which constricted free volume means is operative to receive and axially elongate, by a multiple of at least about four, the extent of substantially all of the white cell and platelet layers, and said body being formed with at least one axially and inwardly tapered end portion which prevents platelet cells from aggregating adjacent to the end surface of said body defined by said end portion.

2. The apparatus of claim 1, wherein said tapered portion of said body is substantially ogival.

3. The apparatus of claim 1, wherein said tapered portion of said body is substantially conical.

* * * * *